US00PP11585P

United States Patent [19]

Zerr

[11] Patent Number: Plant 11,585

[45] Date of Patent: Oct. 17, 2000

[54] POINSETTIA PLANT NAMED 'FISFLIRT SILVER'

[75] Inventor: Katharina Zerr, Simmern, Germany

[73] Assignee: Florfis AG, Binningen, Switzerland

[21] Appl. No.: 09/099,763

[22] Filed: Jun. 19, 1998

[51] Int. Cl.[7] ..... A01H 5/00

[52] U.S. Cl. ..... Plt./306

[58] Field of Search ..... Plt./303, 306, 307

[56] References Cited

U.S. PATENT DOCUMENTS

P.P. 11,139 11/1999 Gross ..... Plt./306

OTHER PUBLICATIONS

GTITM UPOVROM Citation for 'Fisflirt Silver' as per CA PBR 97–1135; Feb. 26, 1997.

GTITM UPOVROM Citation for 'Fisflirt Silver' as per DE PBR EUP00198; Feb. 26, 1997.

GTITM UPOVROM Citation for 'Fisflirt Silver' as per JP PBR 9690; Mar. 27, 1997.

GTITM UPOVROM Citation for 'Fisflirt Silver' as per QZ PBR 980032; Jan. 8, 1998.

*Primary Examiner*—Howard J. Locker
*Assistant Examiner*—Kent L. Bell
*Attorney, Agent, or Firm*—Foley & Lardner

[57] ABSTRACT

The Poinsettia plant 'Fisflirt Silver' is characterized by a light pink bract color; ovate to broad elliptical bracts forming a star-shaped inflorescence; light-green and slightly marbled leaves with irregular white margins; compact and very well-branced plant habit; and a medium to late flowering response.

1 Drawing Sheet

BACKGROUND OF THE INVENTION

The present invention relates to a new and distinct cultivar of Poinsettia plant known by the cultivar name 'Fisflirt Silver', and botanically known as *Euphorbia pulcherrima.*

'Fisflirt Silver' is a naturally occurring, branch mutation of 'Fisflirt' (U.S. Plant Pat. No. 9,385) characterized by bright salmon pink bract color, medium-green foliage and medium-tall plant habit.

A plant partly displaying variegated foliage was discovered by the inventor, Katharina Zerr, among a group of stock plants of the parent cultivar in a greenhouse in Olhao, Portugal, in August 1995.

One branch with white-edged leaves was slightly pinched at the tip in order to induce axillary branches. A few weeks later, the upper part of the original branch, which appeared completely mutated, was cut from the plant and taken to Hillscheid Germany for asexual propagation, which was carried out by planting several stem and stem terminal cuttings. The resulting plants were selected for uniformity of the phenotype before further multiplication.

Horticultural examination initiated in 1996 and continuing thereafter has demonstrated that the combination of characteristics as herein disclosed for 'Fisflirt Silver' are firmly fixed and are retained through successive generations of asexual reproduction.

BRIEF DESCRIPTION OF THE INVENTION

The following traits have been repeatedly observed and are determined to be basic characteristics of 'Fisflirt Silver' which in combination distinguish this poinsettia as a new and distinct cultivar:

1. Light-pink bract color;
2. Ovate bracts forming a tight star-shaped inflorescence;
3. Light-green, slightly marbled leaves with irregular white margins;
4. Low to medium, compact and very well-branched plant habit; and 5. Medium to late flowering response.

'Fisflirt Silver' has not been observed under all possible environmental conditions. The phenotype may vary significantly with variations in environment such as temperature, light intensity, and daylength without, however, any variance in genotype. The following observations, measurements and comparisons describe plants grown in Langley, British Columbia, Canada, under greenhouse conditions which approximate those generally used in commercial practice.

Of the many commercial cultivars known to the inventor, the most similar in comparison to 'Fisflirt Silver' is the parent variety 'Fisflirt'.

In a side by side comparison with 'Fisflirt', 'Fisflirt Silver' has lighter green colored foliage with white edges, a somewhat lighter pink bract color, and more compact plant habit in combination with somewhat slower developing growth characteristics.

BRIEF DESCRIPTION OF THE DRAWING

The accompanying color photographic sheet shows typical inflorescences and foliage of 'Fisflirt Silver' with colors being as true as possible with illustrations of this type. The photograph is a side view of a typical mature potted plant.

DETAILED BOTANICAL DESCRIPTION

In the following description, color references are made to The Royal Horticultural Society Colour Chart. The color values were determined indoors in a north light. The plants described were grown in and observations made in a greenhouse in Langley, British Columbia, Canada, in the Autumn 1997. Rooted cuttings were planted into 15 cm pots on August 1, and these were pinched 18 days later. The minimum temperature was 23° C. early in August, 20° C. from late August to November 15, and 16° C. at the time the plants were finished.

The plants developed flowers under natural short day conditions. Observations and measurements were taken at the begining of flowering.

Classification:

*Botanical.*—*Euphorbia pulcherrima*.

*Commercial.*—'Fisflirt Silver'.

Parentage/origin: Naturally occurring mutation of 'Fisflirt'.

Plant description:

*Form.*—Shrub, self-branching, producing a large number of branches.

*Growth habit.*—Low to medium, and relatively compact habit; height (above soil) is approximately 25.0 cm ('Fisflirt' is 29.5 cm); average number of branches is 9.6.

*Rooting.*—Medium, about 24 days

*Blooming habit.*—Flowering begins under natural short-day conditions in autumn botanically in early December; commercially (bracts sufficiently colored), from early December; flowering response time is about 10–11 weeks, depending on temperature.

Foliage:

*Shape.*—Broad ovate to broad elliptical, weakly lobed, most often with slightly rounded and sometimes asymmetric base, acuminate tip; generally, the shape is not as uniform as that of the parent variety.

*Texture.*—Somewhat rugose, weak veins Margin: Mainly entire, partly with irregular crenation.

*Size.*—Leaf blade length is 12.8 cm; Leaf blade width is 7.5 cm; petiole length is 6.6 cm.

*Color.*—Generally light to medium green with narrow white margin.

*Upper surface.*—Main color is slightly more grayish than R.H.S. 138A–B with small, irregular, light gray-green spots, R.H.S. 191C, between the main area and the margin; the white margin is narrow and irregularly shaped, R.H.S. 155A

*Lower surface.*—Main color is near R.H.S. 138A–B; the white margin is R.H.S. 155A.

*Leaf petiole.*—Light green, R.H.S. 145D, occasionally with slight anthocyanin infusion.

Flowering description:

*Inflorescences.*—Aspect is horizontally or slightly upward, flat or slightly folded.

*Average number of inflorescences.*—8.1; approximately 85% of the branches develop a complete inflorescence.

*Average diameter of inflorescence.*—22.5 cm.

*Bracts, shape.*—Ovate to broad elliptical, occasionally weakly lobed margin may show irregular crenation, rounded base and acuminate tip.

*Number.*—Approximately 9–11 true bracts per inflorescence.

*Texture.*—Surface rugose and often slightly folded.

*Color.*—Light pink, uniform, apart from a slight fading near the edge of primary bracts; upper surface, main color is about R.H.S. 52D-50C (in comparison, the upper surface of 'Fisflirt' is 52C); margin is about R.H.S. 52D-51D; lower surface is about R.H.S. 49A–B.

*Size.*—Largest bract length is 12.4 cm (including petiole) and width is 5.7 cm.

*Postproduction longevity.*—Mature bracts do not change color; under low light conditions, longevity is below average. Under high light conditions, longevity is longer. Good commercial quality will be maintained for about three to four weeks.

*Petiole.*—1–2 cm in length, pink to rose-red colored.

*Cyathia.*—Approximately 10–14 in a narrow cluster, about 25–28 mm in diameter.

*Color.*—Mainly light green, R.H.S. 143C; top is reddish, near R.H.S. 46D; (forms a star-shaped pattern on the top end of the immature cyathium; later forms a ring around the stamens or pistil).

*Retention.*—Good.

*Nectar cups.*—Small to medium, yellow to orange, R.H.S. 30A, often red infused at the margin.

*Disease resistance.*—Leaves and bracts are somewhat susceptible to botrytis.

Reproductive organs:

*Stamens.*—Filaments light brown, infertile, abortive.

*Pistils.*—Style whitish to pink, stigma pink.

*Ovaries.*—Triangular; 3-celled; 3 ovules.

I claim:

1. A new and distinct poinsettia plant named 'Fisflirt Silver', as illustrated and described.

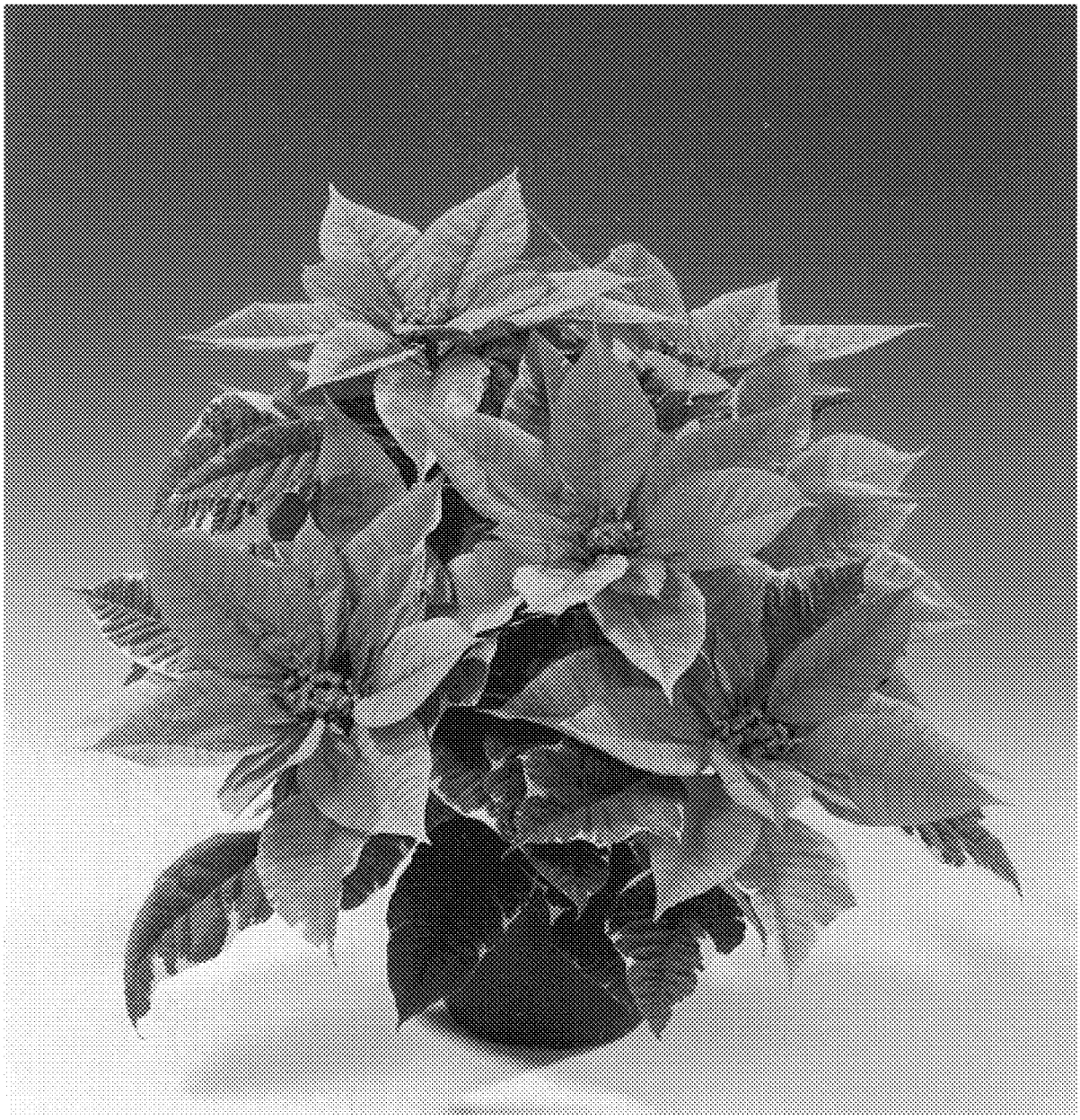

* * * * *